United States Patent
Kim et al.

(10) Patent No.: US 10,307,096 B2
(45) Date of Patent: Jun. 4, 2019

(54) BIOLOGICAL STATE DETERMINING METHOD AND APPARATUS

(71) Applicant: Samsung Electronics Co., Ltd., Suwon-si (KR)

(72) Inventors: Younho Kim, Hwaseong-si (KR); Seungwoo Noh, Seongnam-si (KR); Sangyun Park, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 168 days.

(21) Appl. No.: 15/223,314

(22) Filed: Jul. 29, 2016

(65) Prior Publication Data

US 2017/0035340 A1    Feb. 9, 2017

(30) Foreign Application Priority Data

Aug. 3, 2015  (KR) .................. 10-2015-0109539

(51) Int. Cl.
| | | |
|---|---|---|
| *A61B 5/00* | (2006.01) | |
| *A61B 5/16* | (2006.01) | |
| *A61B 5/0205* | (2006.01) | |
| *G16H 50/30* | (2018.01) | |
| *G16H 50/20* | (2018.01) | |

(52) U.S. Cl.
CPC .......... *A61B 5/165* (2013.01); *A61B 5/0205* (2013.01); *A61B 5/4872* (2013.01); *A61B 5/7246* (2013.01); *G16H 50/20* (2018.01); *G16H 50/30* (2018.01); *A61B 5/6824* (2013.01)

(58) Field of Classification Search
CPC ..... A61B 5/165; A61B 5/0205; A61B 5/7246; A61B 5/4872; A61B 5/6824; G06F 19/34
See application file for complete search history.

(56) References Cited

U.S. PATENT DOCUMENTS

| | | | |
|---|---|---|---|
| 2002/0156351 A1 | 10/2002 | Sagel | |
| 2006/0076025 A1 | 4/2006 | Kim | |
| 2014/0135631 A1* | 5/2014 | Brumback | ......... A61B 5/02438 600/479 |
| 2014/0275854 A1* | 9/2014 | Venkatraman | ......... A61B 5/721 600/301 |

FOREIGN PATENT DOCUMENTS

| | | |
|---|---|---|
| JP | 2008-183048 A | 8/2008 |
| KR | 10-2004-0072526 A | 8/2004 |
| KR | 10-2006-0056843 A | 5/2006 |
| KR | 10-2006-0111887 A | 10/2006 |
| KR | 10-08-17272 B1 | 3/2008 |
| KR | 10-2010-0036085 A | 4/2010 |

* cited by examiner

*Primary Examiner* — Rex R Holmes
(74) *Attorney, Agent, or Firm* — NSIP Law

(57) ABSTRACT

Provided is a biometric state determining method and apparatus. The biometric state determining apparatus may be configured to receive body data and biometric data of a user, and calculate a stress level based on an analysis of the received biometric data. The biometric state determining apparatus may calculate a biometric parameter based on a determined correlation between the calculated stress level and the received body data, and determine a biometric state of the user based on an analysis of the calculated biometric parameter.

27 Claims, 12 Drawing Sheets

BIOLOGICAL STATE DETERMINING METHOD AND APPARATUS

CROSS-REFERENCE TO RELATED APPLICATION(S)

This application claims the benefit under 35 USC 119(a) of Korean Patent Application No. 10-2015-0109539, filed on Aug. 3, 2015 in the Korean Intellectual Property Office, the entire disclosure of which is incorporated herein by reference for all purposes.

BACKGROUND

1. Field

The following description relates to a biological state determining method and apparatus.

2. Description of Related Art

According to westernization and industrialization of our modern society, obesity is increasing gradually among the population. For this reason, various methods based on, for example, a diet and fitness equipment may abound to control weight. Despite the abundance of various methods, many attempts at controlling weight or reaching a target weight end in failure.

As an example, a general weight control method may provide simple information associated with physical body changes such as weight, without providing detailed biometric information.

SUMMARY

This Summary is provided to introduce a selection of concepts in a simplified form that are further described below in the Detailed Description. This Summary is not intended to identify key features or essential features of the claimed subject matter, nor is the Summary intended to be used as an aid in determining the scope of the claimed subject matter.

One or more embodiments provide a biometric state determining method including receiving body data and biometric data of a user, calculating, using at least one processing device, a stress level based on the received biometric data, and determining, using the at least one processing device, a biometric state based on the received body data and the calculated stress level.

The determining of the biometric state may include calculating a biometric parameter based on an analysis of the calculated stress level and the received body data, and determining the biometric state based on an analysis of the calculated biometric parameter.

The determining of the biometric state based on the analysis of the calculated biometric parameter may include determining the biometric state by comparing the calculated biometric parameter to a threshold.

The determining of the biometric state based on the analysis of the calculated biometric parameter may include comparing the calculated biometric parameter to a plurality of thresholds, and determining the biometric state to be one of a plurality of different biometric states based on a result of the comparing.

The calculating of the biometric parameter may include calculating the biometric parameter based on a determined correlation between the calculated stress level and the received body data.

The calculating of the biometric parameter may include calculating the biometric parameter based on a determined difference between the calculated stress level and the received body data.

The determining of the biometric state may include normalizing each of the calculated stress level and the received body data, and determining the biometric state based on a comparison of the normalized stress level and the normalized body data.

The receiving may include sensing at least two types of biometric data, and the calculating may include calculating the stress level based on the at least two types of biometric data.

The calculating of the stress level may include extracting pattern data from the biometric data, and calculating the stress level based on an analysis of the pattern data.

One or more embodiments may provide a non-transitory processor readable medium including processor readable code to control at least one processing device to one or more methods described herein.

One or more embodiments provide a biometric state determining apparatus including a receiver configured to receive body data and biometric data of a user, and at least one processing device configured to calculate a stress level based on the received biometric data and to determine a biometric state based on the received body data and the calculated stress level.

The at least one processing device may be configured to calculate a biometric parameter based on an analysis of the calculated stress level and the received body data, and to determine the biometric state based on an analysis of the calculated biometric parameter.

The at least one processing device may be configured to determine the biometric state by comparing the calculated biometric parameter to a threshold.

The at least one processing device may be configured to compare the calculated biometric parameter to a plurality of thresholds, and to determine the biometric state to be one of a plurality of different biometric states based on a result of the comparing.

The at least one processing device may be configured to calculate the biometric parameter based on a determined correlation between the calculated stress level and the received body data.

The at least one processing device may be configured to calculate the biometric parameter based on a determined difference between the calculated stress level and the received body data.

The at least one processing device may be configured to normalize each of the calculated stress level and the received body data, and to determine the biometric state based on a comparison of the normalized stress level and the normalized body data.

The receiver may be configured to receive at least two types of biometric data, and the at least one processing device may be configured to calculate the stress level based on the at least two types of biometric data.

The at least one processing device may be configured to extract pattern data from the biometric data and calculate the stress level based on an analysis of the pattern data.

The receiver may include a biometric signal sensor configured to sense a biosignal of the user, and the processor may be configured to extract the pattern data from the biosignal.

The apparatus may further include a display configured to display the determined biometric state, and a communicator configured to transmit information of the determined biometric state to an external apparatus.

Other features and aspects will be apparent from the following detailed description, the drawings, and the claims.

Figure 1:
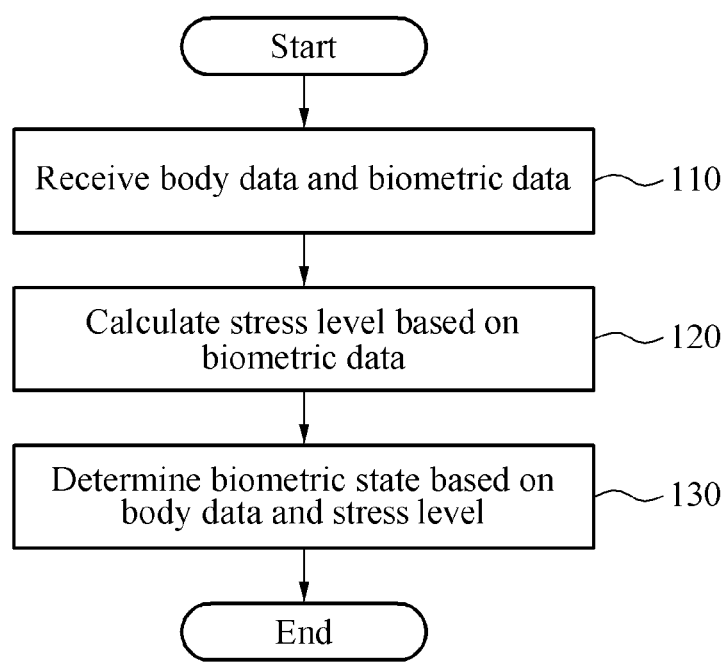
FIG. 1 is a flowchart illustrating a biometric state determining method, in accordance with one or more embodiments.

Throughout the drawings and the detailed description, unless otherwise described or provided, the same drawing reference numerals will be understood to refer to the same or like elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, after an understanding of the present disclosure, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent, after an understanding of the present disclosure, to one of ordinary skill in the art, with the exception of operations necessarily occurring in a certain order. Also, descriptions of functions and constructions that may be well known to one of ordinary skill in the art, after an understanding of the present disclosure, may be omitted for increased clarity and conciseness.

Various alterations and modifications may be made to embodiments, some of which will be illustrated in detail in the drawings and detailed description. However, it should be understood that these embodiments are not construed as limited to the disclosure and illustrated forms and should be understood to include all changes, equivalents, and alternatives within the idea and the technical scope of this disclosure.

Terms used herein are to merely explain specific embodiments, thus it is not meant to be limiting. A singular expression includes a plural expression except when two expressions are contextually different from each other. For example, as used herein, the singular forms "a", "an", and "the" are intended to include the plural forms as well, unless the context clearly indicates otherwise. Herein, a term "include" or "have" are also intended to indicate that characteristics, figures, operations, components, or elements disclosed on the specification or combinations thereof exist. The term "include" or "have" should be understood so as not to pre-exclude existence of one or more other characteristics, figures, operations, components, elements or combinations thereof or additional possibility.

Unless otherwise defined, all terms including technical and scientific terms used herein have the same meaning as commonly understood by one of ordinary skill in the art to which respective embodiments belong. It will be further understood that terms, such as those defined in commonly-used dictionaries, should be interpreted as having a meaning that is consistent with their meaning in the context of the relevant art and the present disclosure and will not be interpreted in an idealized or overly formal sense unless expressly so defined herein.

When describing the examples with reference to the accompanying drawings, like reference numerals refer to like constituent elements and a repeated description related thereto will be omitted. When it is determined detailed description related to a related known function or configuration they may make a purpose of an embodiment unnecessarily ambiguous in describing the embodiment, such a detailed description will be omitted.

As only an example, when providing information for weight management, the provision of additional information may be desired so that an individual can more accurately recognize their biometric state. Accordingly, one or more embodiments may include an apparatus or method that may determine and provide a user such biometric state information.

FIG. 1 is a flowchart illustrating a biometric state determining method, in accordance with one or more embodiments. The biometric state determining method of FIG. 1 is discussed below only as an example, and embodiments are not limited to the same. Similarly, though the biometric state determining method is explained through operation of a biometric state determining apparatus, such as by any of the biometric state determining apparatuses of FIGS. 7-12, embodiments are not limited thereto.

In operation 110, a receiver of a biometric state determining apparatus, as only an example, receives body data and biometric data. The receiver may receive the body data and the biometric data by measuring the body data and the biometric data from a living body of a user, for example. In an embodiment, the receiver wired and/or wirelessly may additionally or alternatively receive the body data and the biometric data from one or more external sensors. In addition, in one or more embodiments, the receiver receives at least two types of biometric data.

The body data is, for example, data about a body of the user. The body data may include data on, for example, weight, body composition, height, and/or an age of the user, as only example different types of body data. Body composition data may be, for example, data associated with a component of the body. For example, the body composition information may include, for example, body fat and body mass index (BMI) information. An item of the body data is not limited thereto.

The biometric data is, for example, data on a biometric aspect or signal of the user. Hereinafter, such a biometric signal is also referred to as a biosignal. The biometric data may include data associated with, for example, an electrocardiogram (ECG) signal, a photoplethysmography (PPG), and blood pressure, as only example different types of biometric data. In an example, the biometric data includes a biometric signal sensitively responding to a sympathetic nerve. An item of the biometric data is not limited thereto.

In operation 120, a processor of the biometric state determining apparatus calculates a stress level based on the biometric data. As an example, the processor calculates a stress level by processing the biometric data. In this example, the processor may calculate the stress level by processing pattern data of an ECG signal. As another example, the processor applies/considers the biometric data to be the stress level. In this example, the processor may apply/consider a blood pressure signal to be the stress level. In an example, the processor extracts pattern data of the biometric data and calculates the stress level based on the pattern data. Further example descriptions related to a method of calculating such a stress level will be provided below with reference to FIGS. 2 and 3.

Also, the processor may calculate the stress level based on at least two types of biometric data. In an embodiment, the processor may calculate the stress level based on, for example, data obtained by linearly or non-linearly combining two types of biometric data, and pattern data extracted from each of the two types of biometric data.

The stress level is an index indicating a degree of stress. For example, an increase in a value of the stress level indicates an increase in an amount of stress by which a user is affected. Also, a decrease in the value of the stress level indicates a decrease in the amount of stress by which the user is affected.

In operation 130, the processor determines a biometric state based on the body data and the stress level. For example, based on a determined correlation between the body data and the stress level, the processor may determine whether the user is in a yo-yo dieting state, i.e., a state where a user's weight may radically increase or rebound after weight loss. For example, the processor may determine that a user is not in a yo-yo dieting state when a weight or a body fat is reduced and a determined amount of stress is maintained, and determine that the user is in the yo-yo dieting state when the weight or the body fat is reduced and the determined amount of stress increases. In an example, the processor may calculate a biometric parameter to determine the biometric state based on the correlation between the stress level and the body data. Further example descriptions related to a method of calculating the biometric parameter will be provided below with reference to FIG. 5, as only an example.

Herein, the biometric state indicates a state of a living body. As an example, a state of a living body of which a weight is reduced and readily increases is referred to as, for example, a weight cycling state. Thus, the weight cycling state indicates a state that a weight is subject to increase. States other than the weight cycling state may be classified as a normal state. In the weight cycling state, cortisol is secreted in the body due to a radical weight loss, causing a fat increase, for example, an abdominal obesity, thereby increasing a risk of heart disease. Thus, it may be beneficial to a user's weight loss plans to avoid the weight cycling state for more consistent or maintained weight loss. A classification of the biometric state is not limited to the foregoing examples. In addition, in an embodiment, based on a degree to which the weight of the living body is subject to increase, the classification may be performed into a first state, and a second state through an nth state, n being an integer greater than or equal to 2. In this example, when the biometric state is close to the first state, there may be a decreased chance of weight gain or weight may be difficult to increase. Conversely, when the biometric state is close to the nth state, there may be a great chance of weight gain or weight may be subject to increase.

A typical cause of failing a weight control plan may be the aforementioned yo-yo syndrome. The yo-yo syndrome may be dependent on the particular body metabolism in which a brain recognizes a usual weight during the weight control and starts an activity to gain weight to exceed the usual weight in response to an extreme weight loss. The biometric state determining apparatus may predict such a yo-yo syndrome, so as to reduce its effect on a user's diet plan. For example, the biometric state determining apparatus may determine a biometric state of a user so that the user select an appropriate exercise intensity to control the user's biometric state, and prevent the yo-yo syndrome from occurring due to diet stresses, thereby leading the user into effective exercise and diet.

Figure 2:
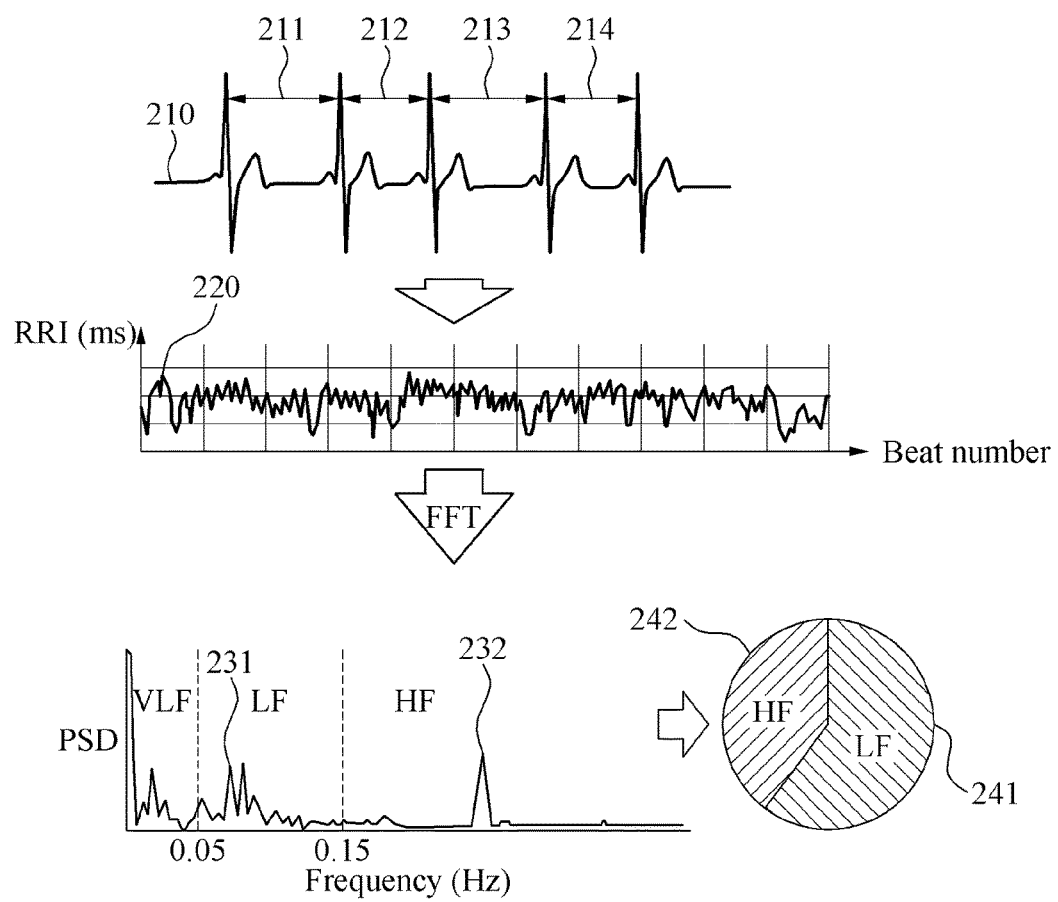
FIGS. 2 and 3 illustrate methods for calculating a stress level, in accordance with one or more embodiments.
Figure 3:
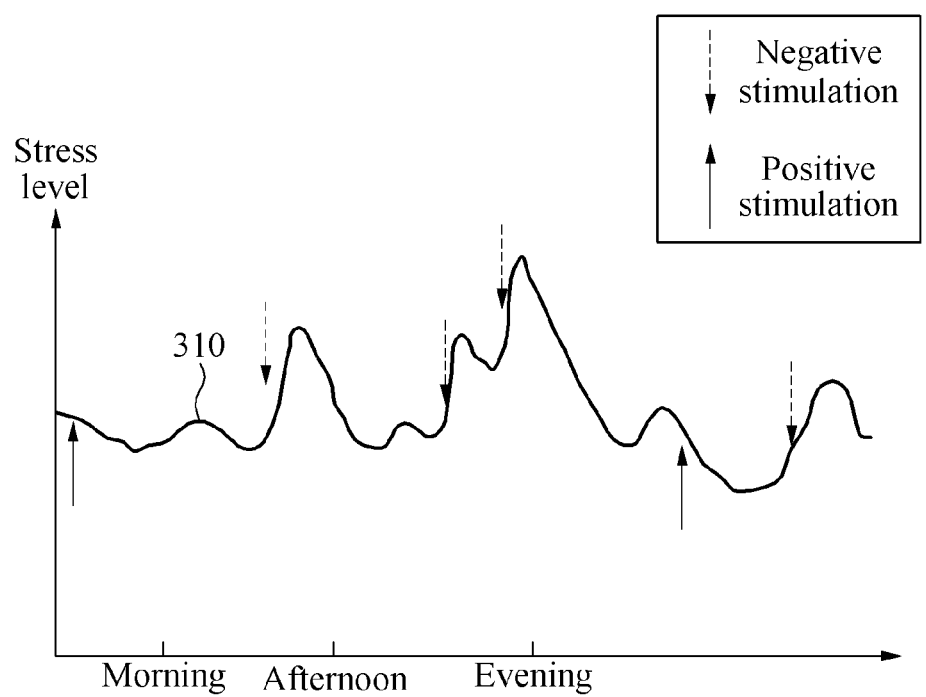

FIGS. 2 and 3 illustrate methods for calculating a stress level, in accordance with one or more embodiments. Here, FIGS. 2 and 3 are used to merely explain how a stress may be calculated in one or more embodiments, as only examples, noting that embodiments are not limited to the same. Similarly, though the stress level calculating method is explained through operation of a processing device(s) of a biometric state determining apparatus, such as by any of the biometric state determining apparatuses of FIGS. 7-12, embodiments are not limited thereto.

The stress level is calculated based on biometric data. Below, as only an example, descriptions related to the biometric data will be provided for FIG. 2 based on an ECG signal.

A processor may be configured to extract pattern data of the biometric data. The pattern data indicates a pattern of the biometric data, for example, an interval between peaks, or other pattern data of the biometric data. In an example, the processor may extract intervals 211, 212, 213, and 214 between peaks based on a signal 210, for example, the ECG signal of the biometric data.

Thus, in this example, the processor may be configured to generate pattern data 220 indicating an interval between peaks extracted for each period of the signal 210 of the biometric data. Here, the pattern data 220 is, for example, an R-to-R interval (RRI) between a peak R and another peak R in the ECG signal, and the period corresponds to, for example, a beat in the ECG signal. Referring to FIG. 2, in the graph representing the RRI 220, the y axis indicates a value corresponding to each of the intervals 211, 212, 213, and 214 between the peaks for each beat, and the x axis indicates the sequential number of beats.

In an example, a slight change in the RRI 220 depends on an activity pattern of an autonomic nervous system, for example, a sympathetic nervous system and a parasympathetic nervous system. As an example, in response to a stimulation applied to the sympathetic nervous system, a response time may be delayed about five seconds when compared to the parasympathetic nervous system. Thus, since the sympathetic nervous system is represented by an example slow RRI pattern and the parasympathetic nervous system is represented by an example fast RRI pattern, the sympathetic nervous system may be represented as a low frequency component of the pattern data 200 and the parasympathetic nervous system may be represented as a high frequency component of the pattern data 200.

Accordingly, the processor may be configured to calculate the stress level based on the pattern data 200. The processor may transform the pattern data 200, for example, the RRI, collected for a predetermined period of time, for example, a number of hours or days, to a frequency domain through, for example, a fast Fourier transform (FFT). As shown by the illustrated power spectral density (PSD) of the RRI in FIG. 2, the RRI transformed to the frequency domain is classified into a low frequency (LF) area 231, for example, an area corresponding to a range from 0.05 to 0.15 hertz (Hz), and a high frequency (HF) area 232, for example, an area corresponding to a range exceeding or equal to 0.15 Hz. The LF area 231 represents the response due to the sympathetic nervous system, and the HF area 232 represents the response due to the parasympathetic nervous system. The processor may calculate a ratio between the area 241 obtained by integrating the LF area 231 and the area 242 obtained by integrating the HF area 232.

In an embodiment, the processor may calculate this ratio, for example, the LF/HF, of the area 241 to the area 242, and determine the calculated ratio to be the stress level. The processor may determine the stress level according to the illustrated graph 310 of FIG. 3, for example, by calculating the stress level at an interval of a predetermined period of time. Referring to FIG. 3, the illustrated upward directional arrow indicates that the stress level decreases in response to a positive stimulation applied to a user, and the illustrated downward directional arrow indicates that the stress level increases in response to a negative stimulation applied to the user.

Figure 4:
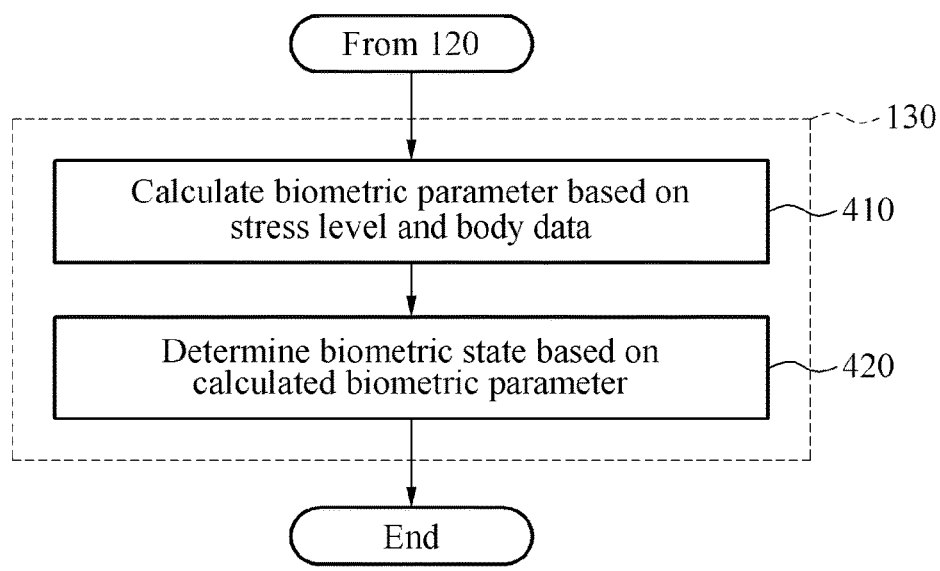
FIG. 4 is a flowchart illustrating a biometric state determining method based on body data and a stress level, in accordance with one or more embodiments.

FIG. 4 is a flowchart illustrating a biometric state determining method based on body data and a stress level, in accordance with one or more embodiments. Here, FIG. 4 is used to merely explain how a biometric state may be determined in one or more embodiments, as only an example, noting that embodiments are not limited to the same. Similarly, though the biometric state determining method is explained through operation of a processing device(s) of a biometric state determining apparatus, such as by any of the biometric state determining apparatuses of FIGS. 7-12, embodiments are not limited thereto.

FIG. 4 is a flowchart illustrating a biometric state determining method based on body data and a stress level, such as performed in operation 130 of FIG. 1, for example.

In operation 410, a processor may calculate a biometric parameter based on a determined stress level and body data. The processor may calculate the biometric parameter based on a determined relationship between the stress level and the body data, such as a determined correlation between the determined stress level and the body data. The correlation between the stress level and the body data indicates, for example, a relationship in terms of an increase and a decrease between the stress level and the body data. The processor may calculate, for example, a difference between the stress level and the body data as the correlation between the stress level and the body data.

Also, to calculate the correlation between the stress level and the body data, the processor may normalize each of the stress level and the body data. The processor may calculate the correlation based on the normalized stress level and the normalized body data. In an embodiment, as described with reference to FIG. 5, the processor may subtract the normalized body data from the normalized stress level to calculate the correlation, represented by the illustrated biometric parameter.

Thus, in operation 420, the processor may determine a biometric state based on the calculated biometric parameter. The processor may determine the biometric state by comparing the biometric parameter to a threshold. As an example, the processor determines that a living body is in a weight cycling state, for example, when the biometric parameter meets, e.g., is greater than, the threshold, and the processor determines that the living body is in a normal state, for example, when the biometric parameter fails to meet, e.g., is less than or equal to, the threshold. Further example descriptions regarding this example biometric parameter are provided below with reference to FIG. 5.

In an embodiment, the processor compares the calculated biometric parameter to a plurality of thresholds. The processor determines the biometric state to be one of a plurality of states. As an example, the processor compares the biometric parameter to a first threshold through an nth threshold, and determines the biometric state to be one of a first state through an nth state based on a result of those comparisons. Further descriptions regarding the plurality of thresholds are provided below with reference to FIG. 6.

Figure 5:
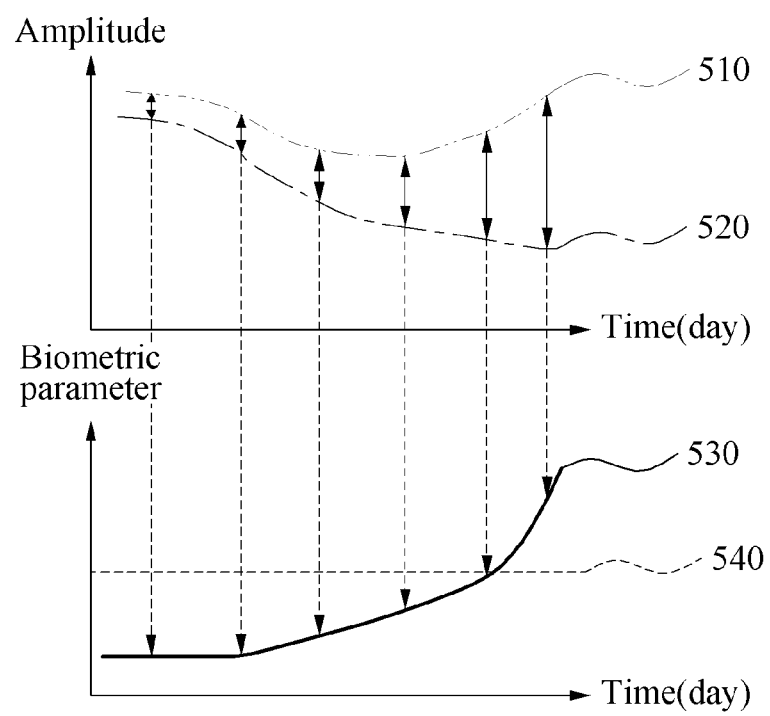
FIG. 5 illustrates a method for calculating a biometric parameter, in accordance with one or more embodiments.

FIG. 5 illustrates a method for calculating a biometric parameter, in accordance with one or more embodiments. Here, FIG. 5 is used to merely explain how a biometric parameter may be determined in one or more embodiments, as only an example, noting that embodiments are not limited to the same. Similarly, though the biometric parameter determining method is explained through operation of a processing device(s) of a biometric state determining apparatus, such as by any of the biometric state determining apparatuses of FIGS. 7-12, embodiments are not limited thereto.

FIG. 5 illustrates a stress level 510 and a body data 520, each being normalized. In an example, a processor divides subsequently collected values of the stress level 510 by an initial value of the stress level 510 and divides subsequently collected body data 520 by an initial value of the body data 520, thereby normalizing each of the stress level 510 and the body data 520. The normalization performed by the processor is not limited to the foregoing example. Thus, the normalization may include any process of transforming the stress level 510 and the body data 520 to the same scale or scales, for example, to be compared in order to extract a correlation between the stress level 510 and the body data 520.

Accordingly, in an embodiment, the processor extracts a biometric parameter 530 from the stress level 510 and the body data 520 through such normalization. For example, as illustrated in FIG. 5, the processor calculates the biometric parameter 530 by subtracting the normalized body data 520 from the normalized stress level 510. The biometric parameter 530 is not limited to the aforementioned example and thus, various formulas expressing the correlation between the stress level 510 and the body data 520 are also applicable thereto. Also, although FIG. 5 illustrates the biometric parameter 530 calculated based on a unit of a day, a unit of the calculated biometric parameter is not limited thereto. Depending on an example, the biometric parameter 530 may be calculated based on various units, for example, at an interval of a predetermined time such as a second, a minute, an hour, and a week.

The processor compares the biometric parameter 530 to the illustrated threshold 540. The processor determines that a living body is in the weight cycling state when the biometric parameter 530 meets, e.g., is greater than, the threshold 540. The processor determines that the living body is in a normal state when the biometric parameter 530 fails to meet, e.g., is smaller than or equal to, the threshold 540. The threshold 540 may be determined through, for example, an experiment, a simulation, and learning. Alternatively, the threshold 540 may be arbitrarily set by a user. Also, the threshold 540 is not limited as a singular form and thus, a plurality of thresholds is also set as described below with reference to FIG. 6.

Figure 6:
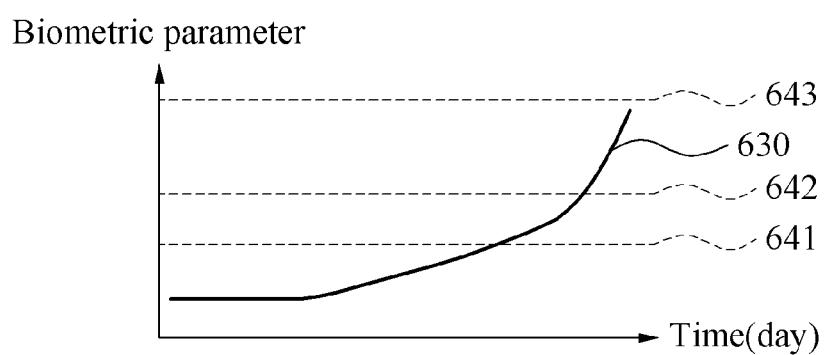
FIG. 6 illustrates a method for comparing a biometric parameter to a plurality of thresholds, in accordance with one or more embodiments.

FIG. 6 illustrates a method for comparing a biometric parameter to a plurality of thresholds, in accordance with one or more embodiments. Here, FIG. 6 is used to merely explain how a biometric parameter may be considered for biometric state determination in one or more embodiments, as only an example, noting that embodiments are not limited to the same. Similarly, though the method of considering such a biometric parameter is explained through operation of a processing device(s) of a biometric state determining apparatus, such as by any of the biometric state determining apparatuses of FIGS. 7-12, embodiments are not limited thereto.

In an embodiment, the processor may compare a biometric parameter 630 to a plurality of thresholds. The processor may determine a biometric state to be a corresponding one of a plurality of states based on a result of the comparing.

As an example, the processor may determine that a user is in a first state when the biometric parameter 630 is smaller than or equal to a first threshold 641. Additionally, the processor may determine that the user is in a second state when the biometric parameter 630 is greater than the first threshold 641 and smaller than or equal to a second threshold 642. Also, the processor may determine that the user is in an nth state when the biometric parameter 630 is greater than an nth threshold 643, n being an integer greater than or equal to 1.

FIGS. 7-10 are block diagrams illustrating biometric state determining apparatuses 700, in accordance with differing embodiments. Here, FIGS. 7-10 merely demonstrate respective non-limiting examples for a biometric state determining apparatus embodiment, noting that alternative embodiments are also available.

Figure 7:
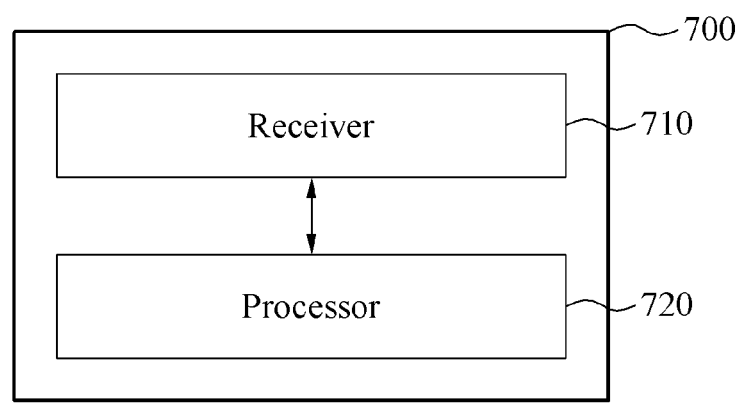
FIGS. 7 through 10 are block diagrams illustrating biometric state determining apparatuses, in accordance with differing embodiments.

The biometric state determining apparatus 700 of FIG. 7 may include a receiver 710 and a processor 720, for example. The processor is hardware that may be a special purpose processor, e.g., configured to implement one or more methods described herein and/or configured to implement or operate based on processor readable code that implements such methods. The processor may also implement or control other processes, such as controlling aspects of the biometric state determining apparatus 700 other than those related to such a determining the aforementioned stress level, correlations, biometric parameter, or biometric state, as only examples.

The receiver 710 may receive or collect body data and biometric data. The receiver 710 may receive the body data and the biometric data wired or wirelessly through, for example, Bluetooth or Zigbee, as only examples.

Figure 8:
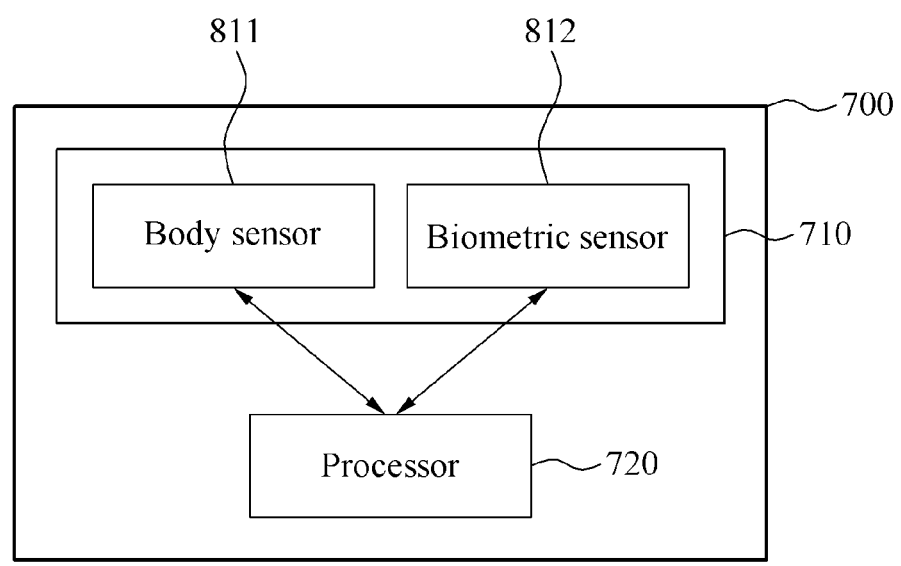

As illustrated in FIG. 8, in the biometric state determining apparatus 700 of FIG. 8, the receiver 710 may include a body sensor 811 and a biometric sensor 812. The body sensor 811 may be configured to receive user body data, for example, through a key input in a user interface of biometric determining apparatus embodiment. Alternatively, the body sensor 811 may be configured to measure user body data, for example, a body fat, and/or other body data. Also, the body sensor 811 may receive or measure a plurality of types of body data. The biometric sensor 812 may measure user biometric data. In an embodiment, for example, the biometric sensor 812 simultaneously measures at least two types of biometric data. For example, the biometric sensor 812 may simultaneously measure an ECG signal and a blood pressure signal, or simultaneously measure other biometric data.

A type of body data received or measured by the body sensor 811 is not limited to the aforementioned examples and thus, the body sensor 811 may input or measure various types of body data depending on embodiment. Also, a type of biometric data measured by the biometric sensor 812 is not limited to the aforementioned example and thus, the biometric sensor 812 measures various types of biometric data depending on embodiment.

Figure 9:
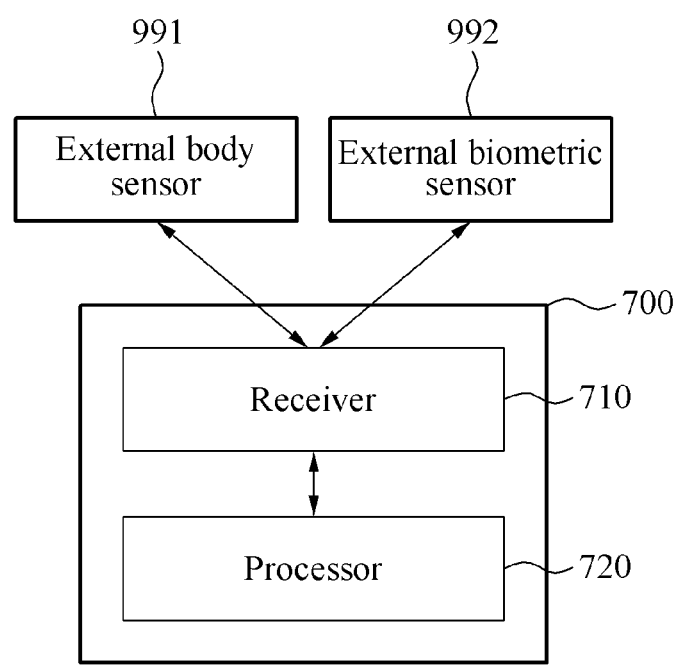

As illustrated in FIG. 9, in the biometric state determining apparatus 700 of FIG. 9, the receiver 710 may wired or wirelessly receive body data and biometric data from an external body sensor 991 and an external biometric sensor 992, respectively, for example. However, embodiments are not limited thereto. For example, in one or more embodiments, the receiver 710 may include the body sensor 811 configured to measure the body data and receive the biometric data from the external biometric sensor 992. The receiver 710 may include the body sensor 811 and also the biometric sensor 812 to measure additional or alternative biometric data and also receive biometric data from the external biometric sensor 992. As another example, in one or more embodiments, the receiver 710 may include the biometric sensor 812 configured to measure the biometric data and receive the body data from the external body sensor 991. The receiver 710 may also include the body sensor 811 to measure or receive additional or alternative body data and the biometric sensor 812 and also receive body data from the external body sensor 991. The receiver 710 may include both body sensor 811 and biometric sensor 812 and receive additional body data or biometric data from the external body sensor 991 and the external biometric sensor 992. In an embodiment, the external body sensor 991 and the external biometric sensor 992 may be implemented as a module device(s) provided independently of the biometric state determining apparatus 700. There may be multiple internal and/or external body and/or biometric sensors.

The processor 720 may calculate a stress level based on the measured or received biometric data, and may determine a biometric state based on the stress level and the body data. Any of the above descriptions related to an operation of calculating the stress level and an operation of determining the biometric state based on the stress level are also applicable and incorporated here with regard to the biometric state determining apparatuses of FIGS. 7-9, as well as with regard to the below biometric state determining apparatus of FIG. 10, biometric state determining scale of FIG. 11, and biometric state determining wearable device of FIG. 12.

Figure 10:
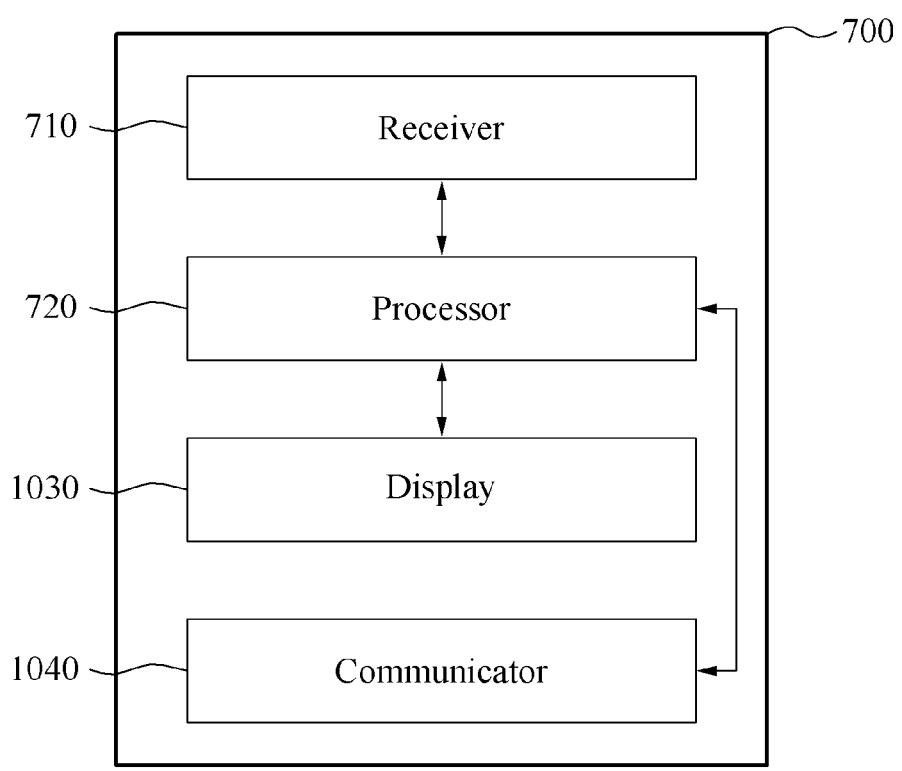

Referring to FIG. 10, the biometric state determining apparatus 700 of FIG. 10 may further includes a display 1030 and/or a communicator 1040, for example.

The display 1030 is hardware that is controlled to display the determined biometric state. For example, the display 1030 may be controlled to display at least one of the biometric data, the body data, the stress level, and the biometric state, e.g., under a control of the processor 720. Thus, when the biometric state is classified into a plurality of states, after observing the displayed information a user may intuitively be able to identify the degree to which a weight cycling phenomenon may be affecting the user's diet plan based on the biometric state displayed on the display 1030. Also, the display 1030 may provide a user interface to control the biometric state determining apparatus 700, or included in a biometric state determining system embodiment.

The communicator 1040 is communication hardware configured to transmit the biometric state externally. As an example, under the control of the processor 720, the communicator 1040 may wired or wirelessly transmit at least one of the body data, biometric data, the stress level, and the biometric state to an external apparatus through, for example, a wireless fidelity (WiFi). The external apparatus may be an apparatus provided independently of the biometric state determining apparatus 700.

Figure 11:
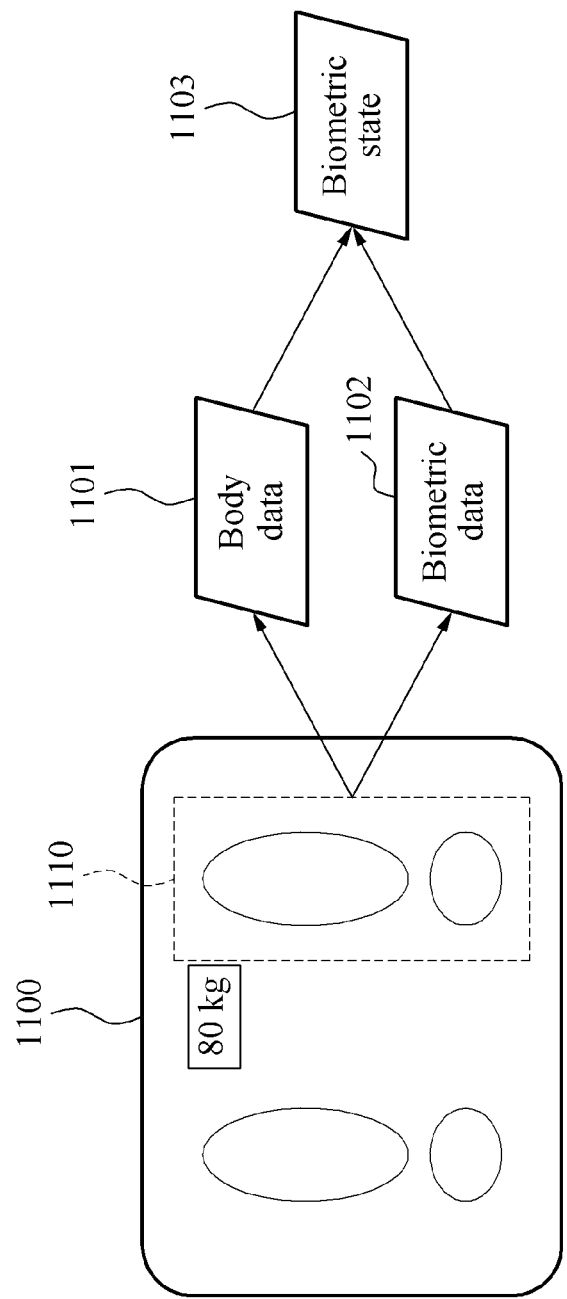
FIG. 11 illustrates a biometric state determining scale, in accordance with one or more embodiments.

FIG. 11 illustrates a biometric state determining scale 1100, in accordance with one or more embodiments.

In an embodiment, the biometric state determining scale 1100 may measure, as only an example, body fat of a user as body data 1101 using a bioelectrical impedance analysis (BIA)-based body sensor of a receiver 1110. The biometric state determining scale 1100 may measure alternative body data. In an embodiment, the receiver 1110 measures an ECG signal of the user as biometric data 1102 using a biometric sensor, as only an example. Although FIG. 11 illustrates the measured weight of the user as 80 kilograms (kg) as an example, the weight may also be expressed using a point representation system, and measured or expressed based on other units, for example, grams (g). Also, a configuration of the receiver 1110 and a type of data measured by the receiver 1110 may vary depending on an implementation. Aspects of the receiver 710 and processor 720 of FIGS. 7-10 are also applicable and incorporated here with regard to the receiver 1110 and processor of the biometric state determining scale 1100.

In an example, when the biometric state determining scale 1100 may receive a command to initiate a biometric state determination, for example, represented by when a user is determined to be located on the biometric state determining scale 1100, the biometric state determining scale 1100 may collect, for example, measurements of a weight, the body fat, and the ECG signal of the user. However, embodiments are not limited thereto. The biometric state determining scale 1100 may not directly measure the weight and the ECG signal and may wired or wirelessly receive a weight and an ECG signal measured by an external sensor, for example.

The biometric state determining scale 1100 determines a biometric state 1103 of the user based on the body data 1101 and the biometric data 1102. As the foregoing, the biometric state determining scale 1100 may determine, for example, whether the user is in a weight cycling state, e.g., by comparing a degree to which the stress level increases based on the biometric data 1120 to a degree to which the weight decreases based on the body data 1101. The determining may include outputting the determined biometric state 1103 to the user with the display of the biometric state determining scale 1100, such with the display that alternatively displays the measured or received weight measurement.

Figure 12:
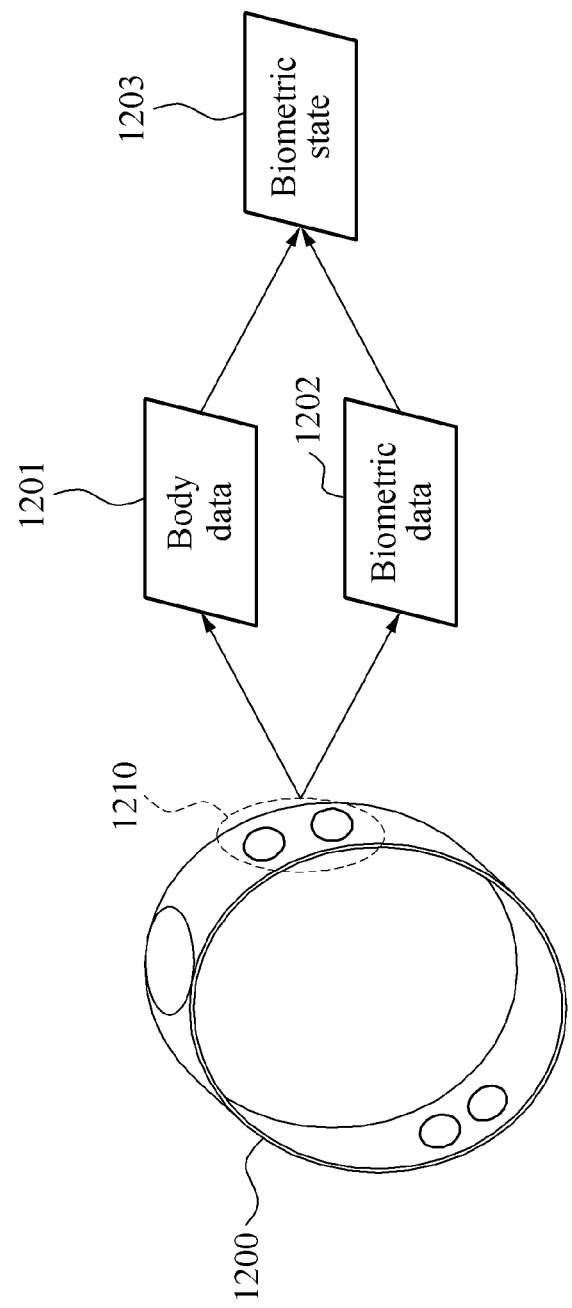
FIG. 12 illustrates a biometric state determining wearable device, in accordance with one or more embodiments.

FIG. 12 illustrates a biometric state determining wearable device 1200, in accordance with one or more embodiments.

As only an example, the biometric state determining wearable device 1200 may be implemented in a form of a wrist band, and the biometric state determining wearable device 1200 may receive a command to initiate a biometric state determination from a user, for example, such as at predetermined times while the user is wearing the wrist band or at select times when the user requests through interaction with the user interface of the biometric state determining wearable device 1200. The wearable device may implemented in other forms. In response to the command, the biometric state determining wearable device 1200 may measure a body fat of the user as body data 1201 based on a BIA through a receiver 1210, as only an example, and measure an ECG signal as biometric data 1202 using an ECG sensor of the receiver 1210, similarly as only an example. As such body data and biometric data and sensors are only examples, embodiments are not limited to such examples. Depending on embodiment, the biometric state determining wearable device 1200 may wired or wirelessly receive the body data 1201 and the biometric data 1202 from an external sensor.

In an example, the biometric state determining wearable device 1200 may calculate a stress level based on the body data 1201 and the biometric data 1202, and determine a biometric state 1203 based on the calculated stress level. Also, the biometric state determining wearable device 1200 may transmit the biometric state 1203 to an external apparatus. Aspects of the receiver 710 and processor 720 of FIGS. 7-10 are also applicable and incorporated here with regard to the receiver 1210 and processor of the biometric state determining wearable device 1200.

In an embodiment, the biometric state determining wearable device 1200 may provide, to a user, biometric state information for predicting a probability of a weight cycling phenomenon, for example, the yo-yo syndrome, indicating the degree to which weight may radically increase in response to current weight loss. The user may be provided the biometric state information through a display of the biometric state determining wearable device 1200 or through display on another electronic device that is provided the biometric state information, in a biometric state determining system embodiment. The biometric state 1203 determined through the aforementioned process may be applied to a health and diet management.

In addition to the elements of FIGS. 7-12 being hardware elements or hardware components, the methods of FIGS. 1-6 may be implemented by such hardware components, including the above discussed example hardware elements and/or one or more processing devices, or processors, or computers, and the elements or components of FIGS. 7-12 may similarly be included in an electronic device embodiment as hardware components thereof. Hardware components may include, as only examples, resistors, transistors, capacitors, inductors, power supplies, controllers, frequency generators, operational amplifiers, power amplifiers, low-pass filters, high-pass filters, band-pass filters, analog-to-digital converters, digital-to-analog converters, and processing device(s), processor(s), and/or computer(s), as only examples. A processing device, processor, or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processing device, processor, or computer includes, or is connected to, one or more memories storing instructions or software that are executed by the processing device, processor, or computer and that may control the processing device, processor, or computer to implement one or more methods described herein. Hardware components implemented by a processing device, processor, or computer may execute instructions or software, such as an operating system (OS) and one or more software applications that run on the OS, to perform or control one or more of the operations described herein with respect to FIGS. 1-6, for example. The hardware components also access, manipulate, process, create, and/or store data in response to execution of the instructions or software. For simplicity, the singular term "processing device", "processor", or "computer" may be used in the description of the examples described herein, but in other examples multiple processing devices, processors, or computers are used, or a processing device, processor, or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, remote processing environments, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing, as only examples.

The methods illustrated in FIGS. 1-6 that perform or control the operations described herein may be performed or controlled by a processing device, processor, or a computer as described above executing instructions or software to perform one or more of the operations described herein.

Instructions or software to control a processing device, processor, or computer to implement the hardware components and perform the methods as described above may be written as computer programs, code segments, instructions or any combination thereof, for individually or collectively instructing or configuring the processing device, processor, or computer to operate as a machine or special-purpose computer to perform the operations performed by the hardware components and the methods as described above. In one example, the instructions or software include machine code that is directly executed by the processing device, processor, or computer, such as machine code produced by a compiler. In another example, the instructions or software include higher-level code that is executed by the processing device, processor, or computer using an interpreter. Based on the disclosure herein, and after an understanding of the same, programmers of ordinary skill in the art may readily write the instructions or software based on the block diagrams and the flow charts illustrated in the drawings and the corresponding descriptions in the specification, which disclose such method operations and which may be performed or implemented by any of the above described hardware components, for example.

The instructions or software to control a processing device, processor, or computer to implement the hardware components, such as discussed in any of FIGS. 7-12, and perform or control the implementation of the methods as described above in FIGS. 1-6, and any associated data, data files, and data structures, are recorded, stored, or fixed in or on one or more non-transitory computer-readable storage media. Examples of a non-transitory computer-readable storage medium include read-only memory (ROM), random-access memory (RAM), dynamic random-access memory (D-RAM), static random-access memory (S-DRAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processing device, processor, or computer so that the processing device, processor, or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processing device, processor, or computer.

As a non-exhaustive example only, and in addition to the above explanation of potential hardware implementations of an electronic device, an electronic device embodiment herein that includes the processor described with regard to FIGS. 1-12, as only an example, may also be a mobile device, such as a cellular phone, a smart phone, a wearable smart biosignal device, a portable personal computer (PC) (such as a laptop, a notebook, a subnotebook, a netbook, or an ultra-mobile PC (UMPC), a tablet PC (tablet), a phablet, a personal digital assistant (PDA), a digital camera, a portable game console, an MP3 player, a portable/personal multimedia player (PMP), a handheld e-book, a global positioning system (GPS) navigation device, or a sensor, or a stationary device, such as a desktop PC, a television or display, a DVD player, a Blu-ray player, a set-top box, or a home appliance, an Internet of Things device, or any other mobile or stationary device, e.g., capable of wireless or network communication, for example, and capable of receiving or sensing/capturing the body data and biometric data, for example, and capable of determining a biometric state based on the received/sensed information, as well capable of informing a user of the determined biometric state, depending on embodiment.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is not limited by the detailed description, but further supported by the claims and their equivalents, and all variations within the scope of the claims and their equivalents are to be construed as being included in the disclosure.

What is claimed is:

1. A processor-implemented method, performed by a computing apparatus in a biometric system, of determining a biometric state for a user, the method comprising:
   receiving, by one or more processors of the computing apparatus, body data of the user from a first sensor;
   measuring, by the one or more processors and using a second sensor, biometric data of the user;
   determining, by the one or more processors, a stress level based on an analysis of extracted pattern data being extracted from the measured biometric data; and
   determining, by the one or more processors, the biometric state based on the received body data and the determined stress level.

2. The method of claim 1, wherein the determining of the biometric state comprises:
   determining a biometric parameter based on an analysis of the determined stress level and the received body data; and determining the biometric state based on an analysis of the determined biometric parameter.

3. The method of claim 2, wherein the determining of the biometric state based on the analysis of the determined biometric parameter further comprises determining the biometric state by comparing the determined biometric parameter to a threshold.

4. The method of claim 2, wherein the determining of the biometric state based on the analysis of the determined biometric parameter further comprises:
comparing the determined biometric parameter to a plurality of thresholds; and
determining the biometric state to be one of a plurality of different biometric states based on a result of the comparing.

5. The method of claim 2, wherein the determining of the biometric parameter further comprises determining the biometric parameter based on a determined correlation between the determined stress level and the received body data.

6. The method of claim 2, wherein the determining of the biometric parameter further comprises determining the biometric parameter based on a determined difference between the determined stress level and the received body data.

7. A processor-implemented method, performed by a computing apparatus in a biometric system, of determining a biometric state for a user, the method comprising:
receiving, by at least one processor of the computing apparatus, body data of the user from a first sensor;
measuring, by the at least one processor and using a second sensor, biometric data of a user;
determining, by the at least one processor, a stress level based on the measured biometric data; and
determining, by the at least one processor, the biometric state based on the received body data and the determined stress level,
wherein the determining of the biometric state comprises:
normalizing each of the determined stress level and the received body data; and
determining the biometric state based on a comparison of the normalized stress level and the normalized body data.

8. A processor-implemented method, performed by a computing apparatus in a biometric system, of determining a biometric state for a user, the method comprising:
receiving, by one or more processors of the computing apparatus, body data of the user from a first sensor;
measuring, by the one or more processors and using a second sensor, biometric data of the user;
determining, by the one or more processors, a stress level based on the measured biometric data; and
determining, by the one or more processors, the biometric state based on the received body data and the determined stress level, wherein the measuring comprises sensing at least two types of biometric data, and the determining of the stress level comprises calculating the stress level based on the at least two types of biometric data.

9. A non-transitory processor readable medium comprising processor readable code to control the one or more processors to implement the method of claim 1.

10. A biometric state determining apparatus in a biometric system, the apparatus comprising:
a receiver configured to receive body data of a user from a first sensor; and
one or more processors configured to:
measuring, using a second sensor, biometric data of the user;
determine a stress level based on an analysis of extracted pattern data being extracted from the measured biometric data; and
determine a biometric state based on the received body data and the determined stress level.

11. The apparatus of claim 10, wherein the one or more processors are further configured to:
determine a biometric parameter based on an analysis of the determined stress level and the received body data; and
determine the biometric state based on an analysis of the determined biometric parameter.

12. The apparatus of claim 11, wherein, for the determining of the biometric state, the one or more processors are further configured to determine the biometric state by comparing the determined biometric parameter to a threshold.

13. The apparatus of claim 11, wherein, for the determining of the biometric state, the one or more processors are further configured to:
compare the determined biometric parameter to a plurality of thresholds; and
determine the biometric state to be one of a plurality of different biometric states based on a result of the comparing.

14. The apparatus of claim 11, wherein, for the determining of the biometric parameter, the one or more processors are further configured to determine the biometric parameter based on a determined correlation between the determined stress level and the received body data.

15. The apparatus of claim 11, wherein, for the determining of the biometric parameter, the one or more processors are further configured to determine the biometric parameter based on a determined difference between the determined stress level and the received body data.

16. The apparatus of claim 10, wherein, for the determining of the biometric state, the one or more processors are further configured to:
normalize each of the determined stress level and the received body data; and
determine the biometric state based on a comparison of the normalized stress level and the normalized body data.

17. A biometric state determining apparatus in a biometric system, the apparatus comprising:
a receiver configured to receive body data of a user from a first sensor; and
one or more processors configured to:
measuring, using a second sensor, biometric data of the user;
determine a stress level based on the measured biometric data; and
determine a biometric state based on the received body data and the determined stress level,
wherein the receiver is further configured to receive at least two types of additional biometric data for the user, and
wherein, for the determining of the stress level, the one or more processors are further configured to determine the stress level based on the at least two types of additional biometric data.

18. The apparatus of claim 10, wherein the receiver comprises a biometric signal sensor configured to sense a biosignal of the user, and the one or more processors are configured to extract the pattern data from the biosignal.

19. The apparatus of claim 10, further comprising:
a display configured to display the determined biometric state; and a communicating processor configured to transmit information of the determined biometric state to an external apparatus.

20. The method of claim 1, wherein the biometric state of the user is determined based on a determined difference between the determined stress level and the received body data.

21. The method of claim 1, wherein the body data is bodily characteristic information of the user distinguished from real time physiological information of the user.

22. The method of claim 21, wherein the determining of the biometric state comprises:
   normalizing each of the determined stress level and the received body data; and
   determining the biometric state based on a comparison of the normalized stress level and the normalized body data.

23. The method of claim 21, wherein the biometric state of the user is determined based on a determined correlation between the determined stress level and the received body data.

24. The method of claim 21, wherein the bodily characteristic information of the user includes one or more of information on the weight, body composition, height, and/or age of the user.

25. The method of claim 24, wherein the biometric data is real time biosignal information of an electrocardiogram (ECG), photoplethysmography (PPG), and/or blood pressure readings.

26. The method of claim 1, wherein the measuring comprises sensing at least two types of biometric data, and the determining of the stress level comprises calculating the stress level based on the at least two types of biometric data.

27. The apparatus of claim 10, wherein the receiver is further configured to receive at least two types of additional biometric data for the user, and
   wherein, for the determining of the stress level, the one or more processors are further configured to determine the stress level based on the at least two types of additional biometric data.

* * * * *